(12) United States Patent
Fingler et al.

(10) Patent No.: US 9,763,569 B2
(45) Date of Patent: Sep. 19, 2017

(54) OPTICAL COHERENCE TOMOGRAPHY (OCT) SYSTEM WITH IMPROVED MOTION CONTRAST

(71) Applicants: UNIVERSITY OF SOUTHERN CALIFORNIA, Los Angeles, CA (US); CALIFORNIA INSTITUTE OF TECHNOLOGY, Pasadena, CA (US)

(72) Inventors: Jeffrey P. Fingler, Orange, CA (US); Scott E. Fraser, Glendale, CA (US)

(73) Assignees: UNIVERSITY OF SOUTHERN CALIFORNIA, Los Angeles, CA (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/104,491

(22) PCT Filed: Feb. 4, 2015

(86) PCT No.: PCT/US2015/014410
§ 371 (c)(1),
(2) Date: Jun. 14, 2016

(87) PCT Pub. No.: WO2015/120017
PCT Pub. Date: Aug. 13, 2015

(65) Prior Publication Data
US 2017/0000327 A1    Jan. 5, 2017

Related U.S. Application Data

(60) Provisional application No. 61/935,428, filed on Feb. 4, 2014.

(51) Int. Cl.
*A61B 3/14*   (2006.01)
*A61B 3/00*   (2006.01)
(Continued)

(52) U.S. Cl.
CPC .......... *A61B 3/0025* (2013.01); *A61B 3/0041* (2013.01); *A61B 3/102* (2013.01);
(Continued)

(58) Field of Classification Search
USPC .................................. 351/200–246
See application file for complete search history.

(56) References Cited

U.S. PATENT DOCUMENTS

2009/0103049 A1    4/2009 McLean et al.
2012/0134563 A1    5/2012 Nakano
(Continued)

FOREIGN PATENT DOCUMENTS

CN    101674770 A    3/2010
CN    102469936 A    5/2012
(Continued)

OTHER PUBLICATIONS

USPTO. 2015. International Search Report and Written Opinion of the US International Searching Authority (ISA/US), dated May 14, 2015, for PCT Application PCT/US2015/014410, entitled "Optical Coherence Tomography (OCT) System with Improved Motion Contrast," of which instant application is a 371 national phase filing.
(Continued)

*Primary Examiner* — Mohammed Hasan
(74) *Attorney, Agent, or Firm* — McDermott Will & Emery LLP

(57) ABSTRACT

This disclosure relates to the field of Optical Coherence Tomography (OCT). This disclosure particularly relates to an OCT system with improved motion contrast. This disclosure particularly relates to motion contrast methods for such OCT systems. The OCT system of this disclosure may have a configuration that scans a physical object, which has a surface and a depth, with a beam of light that has a beam width and a direction; acquires OCT signals from the scan;
(Continued)

forms at least one A-scan using the acquired OCT signals; forms at least one B-scan cluster set using the acquired OCT signals that includes at least two B-scan clusters that each include at least two B-scans. The B-scans within each B-scan cluster set are parallel to one another and parallel to the direction of the beam of light. The OCT system may have a configuration that calculates OCT motion contrast using the at least one B-scan cluster set. This OCT system may form and display an image of the physical object.

27 Claims, 11 Drawing Sheets

(51) Int. Cl.
    *A61B 3/10*         (2006.01)
    *A61B 3/12*         (2006.01)
    *A61B 5/00*         (2006.01)
    *G01B 9/02*         (2006.01)

(52) U.S. Cl.
    CPC .......... *A61B 3/1233* (2013.01); *A61B 5/7203* (2013.01); *G01B 9/02076* (2013.01); *G01B 9/02091* (2013.01); *G01B 2290/65* (2013.01)

(56) References Cited

U.S. PATENT DOCUMENTS

| | | |
|---|---|---|
| 2012/0194783 A1 | 8/2012 | Wei et al. |
| 2012/0274897 A1 | 11/2012 | Narasimha-Iyer et al. |
| 2012/0277579 A1 | 11/2012 | Sharma et al. |
| 2013/0176532 A1 | 7/2013 | Sharma et al. |
| 2013/0301000 A1 | 11/2013 | Sharma et al. |
| 2016/0040977 A1* | 2/2016 | An .................... G01B 9/02077 356/479 |

FOREIGN PATENT DOCUMENTS

| | | |
|---|---|---|
| CN | 103002794 A | 3/2013 |
| WO | 2015/134571 A1 | 9/2015 |

OTHER PUBLICATIONS

Fingler et al., "Mobility and transverse flow visualization using phase variance contrast with spectral domain optical coherence tomography," Optics Express, Optical Society of America, vol. 15, No. 20, Sep. 2007, pp. 21636-12653.

Fingler et al., "Volumetric microvascular imaging of human retina using optical coherence tomography with a novel motion contrast technique," Optics Express, vol. 17, No. 24, Nov. 2009, pp. 22190-22200.

Extended European Search Report from European Patent Application No. 15747055.0 dated Apr. 7, 2017.

An Lin et al., "Using ultrahigh sensitive optical microangiography to achieve comprehensive depth resolved microvasculature mapping for human retina," Journal of Biomedical Optics, Oct. 2011, vol. 16, pp. 106013-1-1060139-9.

Chinese Office Action from Chinese Application No. 201580006935.3, dated May 31, 2017.

* cited by examiner

OPTICAL COHERENCE TOMOGRAPHY (OCT) SYSTEM WITH IMPROVED MOTION CONTRAST

CROSS-REFERENCE TO RELATED APPLICATION

This application is a national phase application of International Application No. PCT/US2015/014410, filed on Feb. 4, 2015, entitled "Optical Coherence Tomography (OCT) System with Improved Motion Contrast"; which is based upon and claims priority to U.S. provisional patent application 61/935,428, entitled "OCT Angiography Enhanced Processing Techniques," filed Feb. 4, 2014. The entire content of both applications is incorporated herein by reference.

STATEMENT REGARDING FEDERALLY SPONSORED RESEARCH

This invention was made with government support under Grant No. NIH STTR 1 R41 EY021054 awarded by National Institutes of Health (NIH). The government has certain rights in the invention.

BACKGROUND

Technical Field

This disclosure relates to the field of Optical Coherence Tomography (OCT). This disclosure particularly relates to an OCT system with improved motion contrast. This disclosure particularly relates to motion contrast methods for such OCT systems.

Description of Related Art

Optical coherence tomography (OCT) has become an indispensable clinical imaging tool, since its introduction in 1991. For a background of OCT technology, see, for example, Drexler and Fujimoto et al. "Optical Coherence Technology: Technology and Applications" Springer, Heidelberg, Germany, 2008. This book is incorporated herein by reference in its entirety. OCT is based on an optical measurement technique known as low-coherence interferometry. OCT performs high resolution, cross-sectional imaging of internal microstructure of a physical object by directing a light beam to the physical object, and then measuring and analyzing magnitude and time delay of backscattered light.

A cross-sectional image is generated by performing multiple axial measurements of time delay (axial scans or A-scans) and scanning the incident optical beam transversely. This produces a two-dimensional data set of A-scans (i.e. B-scans), which represents the optical backscattering in a cross-sectional plane through the physical object. Three-dimensional, volumetric data sets can be generated by acquiring sequential cross-sectional images by scanning the incident optical beam in a raster pattern (three-dimensional OCT or 3D-OCT). This technique yields internal microstructural images of the physical objects with very fine details. For example, pathology of a tissue can effectively be imaged in situ and in real time with resolutions smaller than 15 micrometers.

Several types of OCT systems and methods have been developed, for example, Time-domain OCT (TD-OCT) and Fourier-domain OCT (FD-OCT). Use of FD-OCT enables high-resolution imaging of retinal morphology that is nearly comparable to histologic analysis. Examples of FD-OCT technologies include Spectral-domain OCT (SD-OCT) and Swept-source OCT (SS-OCT).

OCT may be used for identification of common retinovascular diseases, such as age-related macular degeneration (AMD), diabetic retinopathy (DR), and retinovascular occlusions. However, despite the rapid evolution of OCT imaging, current OCT technology may not provide adequate visualization of retinal and choroidal microvasculature. Thus, clinicians are often compelled to order both OCT and fluorescein angiography (FA) in patients with the retinovascular diseases. There has been increased interest in using data generated during FD-OCT imaging to generate angiographic images of the fundus. These angiograms are implemented noninvasively without injection of fluorescent dye.

Recently, phase-variance OCT (PV-OCT) has been introduced to image retinal microvasculature. See, for example, Fingler et al. "Dynamic Motion Contrast and Transverse Flow Estimation Using Optical Coherence Tomography" U.S. Pat. No. 7,995,814; Fingler et al. "Dynamic Motion Contrast and Transverse Flow Estimation Using Optical Coherence Tomography" U.S. Pat. No. 8,369,594; Fingler et al. "Mobility and transverse flow visualization using phase variance contrast with spectral domain optical coherence tomography" Opt. Express 2007; 15:12636-53; Fingler et al. "Phase-contrast OCT imaging of transverse flows in the mouse retina and choroid" Invest Ophthalmol. Vis. Sci. 2008; 49:5055-9; Fingler et al. "Volumetric microvascular imaging of human retina using optical coherence tomography with a novel motion contrast technique" Opt. Express 2009; 17:22190-200; Kim et al. "In vivo volumetric imaging of human retinal circulation with phase-variance optical coherence tomography" Biomed Opt Express [serial online] 2011; 2:1504-13; Kim et al. "Noninvasive imaging of the foveal avascular zone with high-speed, phase-variance optical coherence tomography" Invest. Ophthalmol. Vis. Sci. 2012; 53:85-92; and Kim et al. "Optical imaging of the chorioretinal vasculature in the living human eye" PNAS, Aug. 27, 2013, vol. 110, no. 35, 14354-14359. All these publications and patent disclosures are incorporated herein by reference in their entirety.

PV-OCT uses software processing of data normally acquired, but not used, during FD-OCT imaging. With a different scanning protocol than found in commercial instruments, PV-OCT identifies regions of motion between consecutive B-scans that are contrasted with less mobile regions. In the retina and choroid, the regions with motion correspond to the vasculature; these vessels are readily differentiated from other retinal tissues that are relatively static.

An alternative method to acquire images of the retinal vasculature is Doppler OCT, which measures the change in scatterer position between successive depth scans and uses this information to calculate the flow component parallel to the imaging direction (called axial flow). Doppler OCT has been used to image large axial flow in the retina, but without dedicated scanning protocols this technique is limited in cases of slow flow or flow oriented transverse to the imaging direction. Because this technique depends on measuring motion changes between successive depth scans, as imaging speed improvements continue for FD-OCT systems, the scatterers have less time to move between measurements and the slowest motions become obscured by noise. This further reduces the visualization capabilities of typical Doppler OCT techniques.

In contrast, PV-OCT will be able to achieve the same time separations between phase measurements with increased FD-OCT imaging speeds, maintaining the demonstrated ability to visualize fast blood vessel and slow microvascular flow independently of vessel orientation.

Several groups in recent years have developed OCT imaging methods to push beyond conventional Doppler OCT imaging limitations. Some approaches involve increasing the flow contrast through hardware modifications of FD-OCT machines, such as in 2-beam scanning, or producing a heterodyne frequency for extracting flow components. Other investigators have used nonconventional scanning patterns or repeated B-scan acquisitions, such as used in PV-OCT to increase the time separation between phase measurements and enhance Doppler flow contrast of microvascular flow. In addition to phase-based contrast techniques to visualize vasculature, intensity-based visualization of microvasculature has been developed for OCT using segmentation, speckle-based temporal changes, decorrelation-based techniques, and contrast based on both phase and intensity changes. Each of these methods has varying capabilities in regard to microvascular visualization, noise levels, and artifacts while imaging retinal tissues undergoing typical motion during acquisition. Some of the noise and artifact limitations can be overcome with selective segmentation of the volumetric data or increased statistics through longer imaging times, but further analysis is required to be able to compare all of the visualization capabilities from all these different systems.

For further description of OCT methods and systems, and their applications, for example, see: Schwartz et al. "Phase-Variance Optical Coherence Tomography: A Technique for Noninvasive Angiography" American Academy of Ophthalmology, Volume 121, Issue 1, January 2014, Pages 180-187; Sharma et al. "Data Acquisition Methods for Reduced Motion Artifacts and Applications in OCT Angiography" U.S. Pat. No. 8,857,988; Narasimha-Iyer et al. "Systems and Methods for Improved Acquisition of Ophthalmic Optical Coherence Tomography Data" U.S. Patent Application Publication No. 2014/0268046; Everett "Methods for Mapping Tissue With Optical Coherence Tomography Data" U.S. Pat. No. 7,768,652. All these publications and patent disclosures are incorporated herein by reference in their entirety.

SUMMARY

This disclosure relates to the field of Optical Coherence Tomography (OCT). This disclosure particularly relates to an OCT system with improved motion contrast. This disclosure particularly relates to motion contrast methods for such OCT systems.

The optical coherence tomography (OCT) system may have a configuration that scans a physical object, which has a surface and a depth, with a beam of light that has a beam width and a direction; acquires OCT signals from the scan; and forms at least one B-scan cluster set using the acquired OCT signals.

Each B-scan cluster set may include at least two B-scan clusters. Each B-scan cluster may include at least two B-scans. The B-scans within each B-scan cluster set are parallel to one another and parallel to the direction of the beam of light.

Each B-scan, each B-scan cluster, and each B-scan cluster set are formed at a different time than all other B-scans, B-scan clusters, and B-scan cluster sets, respectively. That is, they are formed over a period of time. In this disclosure, "first formed" means first formed in time; "next formed" or "proximate" means next formed in time; and "last formed" means last formed in time.

Each B-scan within each B-scan cluster may be separated from any next formed B-scan within that B-scan cluster by a distance ("intra-cluster distance") in the range of 0 to half of the beam width. The last formed B-scan within each B-scan cluster may be separated from the first formed B-scan within any next formed B-scan cluster ("inter-cluster distance") by at least one micrometer.

The optical coherence tomography (OCT) system may also have a configuration that uses all or a fraction of the B-scans within each B-scan cluster set to calculate OCT motion contrast for each B-scan cluster set. The optical coherence tomography (OCT) system may also have a configuration that registers the calculated OCT motion contrast as the OCT motion contrast of one of the B-scan clusters within each B-scan cluster set.

The OCT system may also have a configuration that forms at least two B-scan cluster sets parallel to one another using the acquired OCT signals.

The last formed B-scan of one of the B-scan clusters of each B-scan cluster set may be separated from first formed B-scan of one of the B-scan clusters of next formed B-scan cluster set ("inter-cluster-set distance") by at least one micrometer.

The last formed B-scan of one of the B-scan clusters of each B-scan cluster set may be separated from the first formed B-scan of the next formed B-scan cluster set ("inter-cluster-set distance") by at least one micrometer.

The last formed B-scan of first formed B-scan cluster of each B-scan cluster set is separated from the first formed B-scan of the next formed B-scan cluster set ("inter-cluster-set distance") by at least one micrometer.

The last formed B-scan of each B-scan cluster set may be separated from the first formed B-scan of the next formed B-scan cluster set ("inter-cluster-set distance") by at least one micrometer.

The number of B-scan clusters within each B-scan cluster set may be 2, 3 or 4.

The OCT system may have a configuration that uses all of the B-scans within all of the B-scan clusters to calculate the OCT motion contrast. The OCT system may also a configuration that uses all of the B-scans within at least one of the B-scan clusters and only a fraction of the B-scans within at least one other of the B-scan clusters to calculate the OCT motion contrast.

The inter-cluster distance may be no more than 50 micrometers or 100 micrometers. The inter-cluster-set distance may be no more than 50 micrometers or 100 micrometers.

The OCT system may have a configuration that reduces one or more effects of noise on OCT motion contrast by using a thresholding method or a weighting method before calculating the OCT motion contrast.

The thresholding method may include forming pairs of sequentially formed B-scans within one of the B-scan clusters; identifying the B-scan pair that has highest overall motion noise, phase noise, or decorrelation as compared to that of the other B-scan pairs; and removing a data point that has the highest overall motion noise, phase noise, or decorrelation from the calculation of the OCT motion contrast.

The thresholding method may also include forming pairs of proximate B-scans within one of the B-scan clusters; forming pairs of A scans at the same location on a plane parallel to the direction of the beam of light, each member of the pair being selected from a different B scan; identifying the A-scan pair that has the highest overall motion noise, phase noise, or decorrelation as compared to that of other A-scan pairs; and removing data points of the identified A-scan pair from the calculation of the OCT motion contrast.

The thresholding method may also include comparing changes among data points in each B scan cluster that are sequentially acquired at the same location on a plane parallel to the direction of the beam; identifying at least one data point that has the highest noise as compared to the other data points acquired at the same location on the plane within each B-scan cluster; and removing the identified at least one data point from the calculation of the OCT motion contrast.

The thresholding method may also include calculating intensities of two sequentially formed B-scans within a B-scan cluster; calculating a minimum value or an average value of the intensities; identifying at least one data point that has an average value or a minimum value of intensities from the two sequentially formed B-scans which is lower than a thresholding value; and removing the at least one identified data point from the calculation of OCT motion contrast.

The thresholding method may also include comparing changes among data points in each B scan cluster that are sequentially acquired at the same location on a plane parallel to the direction of the beam; identifying at least one data point that has the highest noise as compared to the other data points acquired at the same location on the plane within each B-scan cluster; and removing the identified at least one data point from the calculation of the OCT motion contrast.

The thresholding method may also include calculating intensities of two sequentially formed B-scans within a B-scan cluster; calculating a minimum value or an average value of the intensities; identifying at least one data point that has an average value or a minimum value of intensities from the two sequentially formed B-scans which is lower than a thresholding value; and removing the at least one identified data point from the calculation of OCT motion contrast.

The OCT system may have a configuration that uses the weighting method and wherein the weighting method includes reducing effects of at least one noisy B-scan cluster by using a weighting criterion.

The OCT system may have a configuration that uses the weighting method before calculating the OCT motion contrast and wherein the weighting method includes using at least one B-scan or at least one A-scan within a B-scan cluster, thereby identifying noisy data, and reducing one or more effects of the noisy data by using a weighting criterion.

The OCT system may have a configuration that uses the calculated OCT motion contrast to form an image of the physical object.

The physical object may be human tissue.

The OCT system may have a configuration that identifies regions of motion based on intensity or phase variations between the B-scans. The regions of motion may be identified by using a Phase Variance OCT (PV-OCT) method, a Phase Contrast OCT (PC-OCT) method, an Intensity/Speckle Variance OCT (IV-OCT) method, a Doppler OCT (D-OCT) method, a Power of Doppler Shift OCT (PDS-OCT) method, a Split Spectrum Amplitude Decorrelation Analysis (SSADA) method, an Optical Micro-angiography (OMAG) method, a Correlation Mapping OCT (cmOCT) method, or a combination thereof. The regions of motion may also be identified by using a Phase Variance OCT (PV-OCT) method.

The OCT system may comprise at least one light source that provides that provides the beam of light; at least one retro-reflector; at least one optical fiber coupler or at least one free space coupler that guides the beam of light to the physical object and to at least one retro-reflector, wherein the beam of light guided to the physical object forms at least one backscattered light beam, and wherein the beam of light guided to the at least one retro-reflector forms at least one reflected reference light beam; at least one scanning optic that scans the at least one light beam over the physical object; at least one detector. The at least one detector may combine the at least one backscattered light beam and the at least one reflected light beam to form light interference, detect magnitude and time delay of the at least one backscattered light beam, and forms at least one OCT signal. The at least one optical fiber coupler or the at least one free space coupler may guide the at least one backscattered light beam and the at least one reflected light beam to the at least one detector. The OCT system may further comprise at least one processor that obtains and analyzes the at least one OCT signal formed by the at least one detector, and forms an image of the physical object. The OCT system may also further comprise at least one display that displays the image of the physical object.

A non-transitory, tangible, computer-readable storage media containing a program of instructions that causes a computer system running the program of instructions to function as an optical coherence tomography (OCT) system ("storage media") is also within the scope of this disclosure.

The storage media may have a configuration that scans a physical object, which has a surface and a depth, with a beam of light that has a beam width and a direction; acquires OCT signals from the scan; and forms at least one B-scan cluster set using the acquired OCT signals. Each B-scan cluster set may include at least two B-scan clusters. Each B-scan cluster may include at least two B-scans. The B-scans within each B-scan cluster set are parallel to one another and parallel to the direction of the beam of light. Each B-scan, each B-scan cluster, and each B-scan cluster set are formed at a different time than all other B-scans, B-scan clusters, and B-scan cluster sets, respectively. That is, they are formed over a period of time. In this disclosure, "first formed" means first formed in time; "next formed" means next formed in time; and last formed" means last formed in time. Each B-scan within each B-scan cluster may be separated from any next formed B-scan within that B-scan cluster by a distance ("intra-cluster distance") in the range of 0 to half of the beam width. The last formed B-scan within each B-scan cluster may be separated from the first formed B-scan within any next formed B-scan cluster ("inter-cluster distance") by at least one micrometer.

The storage media may also have a configuration that uses all or a fraction of the B-scans within each B-scan cluster set to calculate OCT motion contrast for each B-scan cluster set. The optical coherence tomography (OCT) system may also have a configuration that registers the calculated OCT motion contrast as the OCT motion contrast of one of the B-scan clusters within each B-scan cluster set.

The storage media may also have a configuration that forms at least two B-scan cluster sets parallel to one another using the acquired OCT signals. The last formed B-scan of one of the B-scan clusters of each B-scan cluster set may be separated from first formed B-scan of one of the B-scan clusters of next formed B-scan cluster set ("inter-cluster-set distance") by at least one micrometer. The last formed B-scan of one of the B-scan clusters of each B-scan cluster set may be separated from the first formed B-scan of the next formed B-scan cluster set ("inter-cluster-set distance") by at least one micrometer. The last formed B-scan of first formed B-scan cluster of each B-scan cluster set is separated from the first formed B-scan of the next formed B-scan cluster set ("inter-cluster-set distance") by at least one micrometer. The last formed B-scan of each B-scan cluster set may be separated from the first formed B-scan of the next formed B-scan cluster set ("inter-cluster-set distance") by at least one micrometer.

The program of instructions may cause the computer system running the program of instructions to: obtain and analyze at least one of the OCT signals; form an image of the physical object; and display the image of the physical object.

Any combination of methods, devices, systems, and features disclosed above are within the scope of this disclosure.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION OF ILLUSTRATIVE EMBODIMENTS

Figure 1:
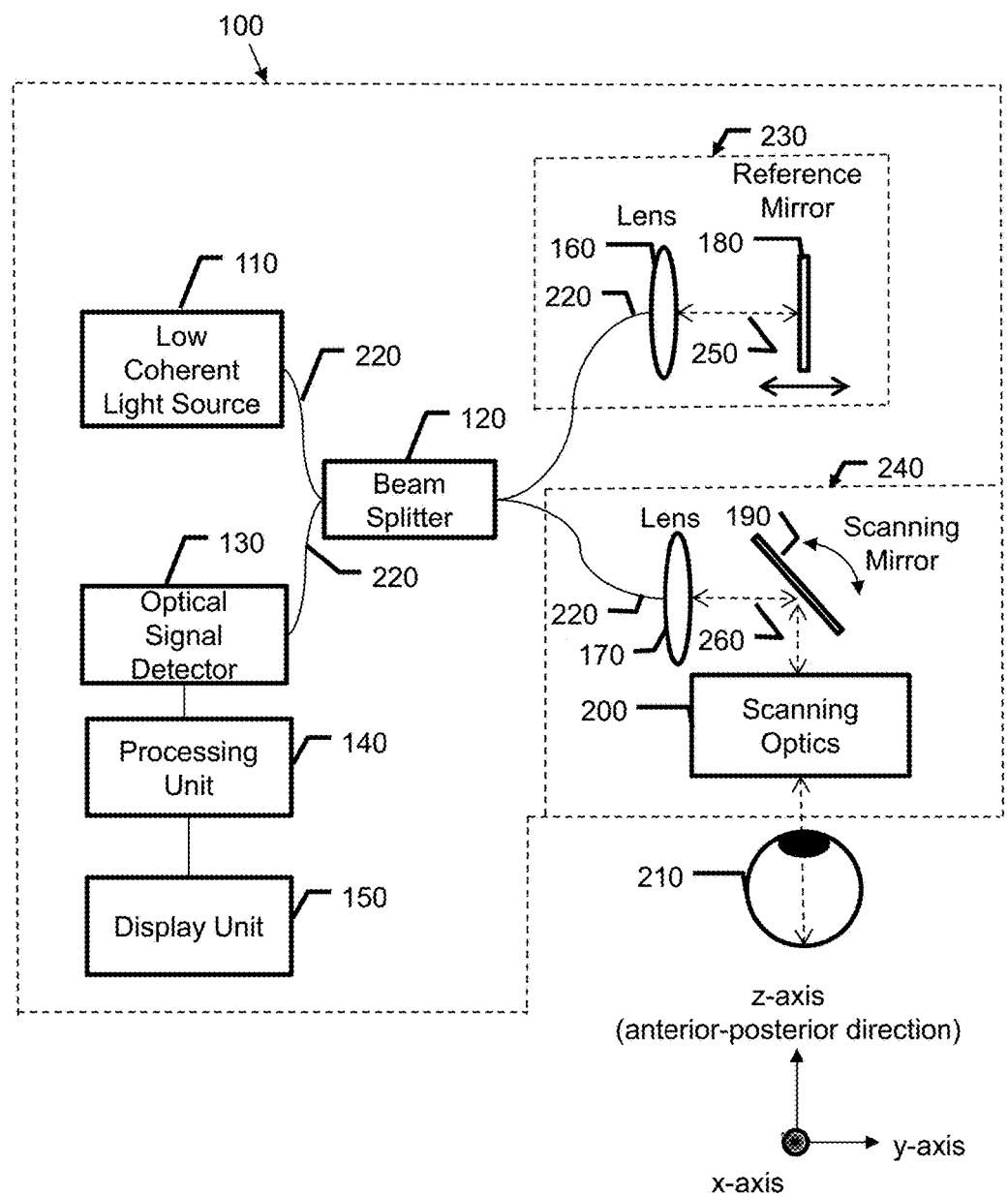
FIG. 1 illustrates a generalized OCT system.

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

This disclosure relates to the field of Optical Coherence Tomography (OCT). This disclosure particularly relates to an OCT system with improved motion contrast. This disclosure particularly relates to motion contrast methods for such OCT systems.

The OCT systems of this disclosure may provide images, at increased processing speeds, with contrasts similar to or better than those of prior-art OCT systems. These OCT systems may also provide images with contrasts better than those of prior-art systems at similar processing speeds. Thus, these OCT systems may provide desired images at reduced processing time and/or better images at typical processing time as compared to the prior-art OCT systems.

This disclosure relates to an OCT system. The OCT system may comprise any interferometer that have optical designs, such as Michelson interferometer, Mach-Zehnder interferometer, Gires-Tournois interferometer, common-path based designs, or other interferometer architectures. The sample and reference arms in the interferometer may consist of any type of optics, for example bulk-optics, fiber-optics, hybrid bulk-optic systems, or the like.

The OCT system may also comprise any OCT system. Examples of the OCT systems may include Time-domain OCT (TD-OCT) and Fourier-domain, or Frequency-domain, OCT (FD-OCT). Examples of the FD-OCT may include Spectral-domain OCT (SD-OCT), Swept Source OCT (SS-OCT), and Optical frequency domain Imaging (OFDI).

The OCT system may use any OCT approaches that identifies and/or visualizes regions of motion ("OCT motion contrast approach"). The OCT motion contrast approach may use motion occurring within the physical object to identify and/or visualize regions with improved contrast. For example, variation of OCT signals caused by blood flow in blood vessels may be used by OCT to identify and/or visualize retinal or choroidal vasculature in the eye through the OCT motion contrast approach. As a result, structures and functions can be visualized that cannot be identified through a typical OCT system. For example, choriocapillaris may become visible by using the OCT motion contrast method. Examples of the OCT motion contrast method may include Phase Variance OCT (PV-OCT), Phase Contrast OCT (PC-OCT), Intensity/Speckle Variance OCT (IV-OCT), Doppler OCT (D-OCT), Power of Doppler Shift OCT (PDS-OCT), Split Spectrum Amplitude Decorrelation Analysis (SSADA), Optical Micro-angiography (OMAG), Correlation Mapping OCT (cmOCT), and the like. Examples of the PV-OCT method are disclosed by Fingler et al. "Dynamic Motion Contrast and Transverse Flow Estimation Using Optical Coherence Tomography" U.S. Pat. No. 7,995,814; Fingler et al. "Dynamic Motion Contrast and Transverse Flow Estimation Using Optical Coherence Tomography" U.S. Pat. No. 8,369,594; Fingler et al. "Mobility and transverse flow visualization using phase variance contrast with spectral domain optical coherence tomography" Opt. Express [serial online] 2007; 15:12636-53; examples of the Speckle Variance OCT method are disclosed by Mariampillai et al. "Speckle variance detection of microvasculature using swept-source optical coherence tomography," Opt. Lett. 33(13), 1530-1532 (2008); examples of the Correlation Mapping OCT method are disclosed by Enfield et al. "In vivo imaging of the microcirculation of the volar forearm using correlation mapping optical coherence tomography (cmOCT)" Biomed. Opt. Express 2, 1184-1193 (2011); examples of the OMAG method are disclosed by An et al. "In vivo volumetric imaging of vascular perfusion within human retina and choroids with optical micro-angiography" Opt. Express 16, 11438-11452 (2008); examples of the Power Doppler OCT method are disclosed by Makita et al. "Optical coherence angiography" Opt. Express 14, 7821-7840 (2006); examples of the SSADA method are disclosed by Jia et al. "Split-spectrum amplitude-decorrelation angiography with optical coherence tomography," Opt. Express 20(4), 4710-4725 (2012). Entire contents of these disclosures are incorporated herein by reference.

The OCT system 100 may comprise at least one light source 110, at least one scanning optic 200, at least one retro-reflector 180, at least one optical fiber coupler 220 or at least one free space coupler, at least one detector 130, at least one processing unit 140, and at least one display unit 150.

Examples of a generalized OCT system schematically shown in FIG. 1 are disclosed by Fingler et al. "Dynamic Motion Contrast and Transverse Flow Estimation Using Optical Coherence Tomography" U.S. Pat. No. 7,995,814; Fingler et al. "Dynamic Motion Contrast and Transverse Flow Estimation Using Optical Coherence Tomography" U.S. Pat. No. 8,369,594; and Sharma et al. in a U.S. Pat. No. 8,857,988, entitled "Data Acquisition Methods for Reduced Motion Artifacts and Applications in OCT Angiography". These disclosures are incorporated herein by reference in their entirety. The OCT system 100 may comprise this generalized OCT system.

The at least one light source 110 may comprise any light source, for example, a low coherent light source. Light from the light source 110 may be guided, typically by using at least one optical fiber 220 to illuminate a physical object 210. An example of the physical object 210 may be any tissue in a human eye. For example, the tissue may be a retina. The light source 110 may be either a broadband low coherence light source with short temporal coherence length in the case of SD-OCT or a wavelength tunable laser source in the case of SS-OCT. The light may be scanned, typically with the scanning optic 200 between the output of the optical fiber 220 and the physical object 210, so that a beam of light (dashed line) guided for the physical object 210 is scanned laterally (in x-axis and/or y-axis) over the area or volume to be imaged. The scanning optic 200 may comprise any optical element suitable for scanning. The scanning optic 200 may comprise at least one component. The at least one component of the scanning optic 200 may be an optical component. Light scattered from the physical object 210 may be collected, typically into the same optical fiber 220 used to guide the light for the illumination of the physical object 210. (The physical object 210 is shown in FIG. 1 only to schematically demonstrate the physical object 210 in relation to the OCT system 100. The physical object 210 is not a component of the OCT system 100.)

The OCT system 100 may further comprise a beam splitter 120 to split and guide the light provided by the light source 110 to a reference arm 230 and a physical object arm 240. The OCT system may also further comprise a lens 160 placed between the beam splitter 120 and the retro-reflector 180. The OCT system may also further comprise another lens 170 placed between the beam splitter 120 and the scanning optic 200.

Reference light 250 derived from the same light source 110 may travel a separate path, in this case involving the optical fiber 220 and the retro-reflector 180 with an adjustable optical delay. The retro-reflector 180 may comprise at least one component. The at least one component of the retro-reflector 180 may be an optical component, for example, a reference mirror. A transmissive reference path may also be used and the adjustable delay may be placed in the physical object arm 240 or the reference arm 230 of the interferometer 100.

Collected light 260 scattered from the physical object 210 may be combined with reference light 250, typically in the fiber coupler to form light interference in the detector 130. Although a single optical fiber port is shown going to the detector 130, various designs of interferometers may be used for balanced or unbalanced detection of the interference signal for SS-OCT or a spectrometer detector for SD-OCT.

The output from the detector 130 may be supplied to the processor 140. Results may be stored in the processor 140 or displayed on the display 150. The processing and storing functions may be localized within the OCT system or functions may be performed on an external processing unit to which the collected data is transferred. This external unit may be dedicated to data processing or perform other tasks that are quite general and not dedicated to the OCT system.

Light beam as used herein should be interpreted as any carefully directed light path. In time-domain systems, the reference arm 230 may need to have a tunable optical delay to generate interference. Balanced detection systems may typically be used in TD-OCT and SS-OCT systems, while spectrometers may be used at the detection port for SD-OCT systems.

The interference may cause the intensity of the interfered light to vary across the spectrum. The Fourier transform of the interference light may reveal the profile of scattering intensities at different path lengths, and therefore scattering as a function of depth (z-axis direction) in the physical object. See for example Leitgeb et al. "Ultrahigh resolution Fourier domain optical coherence tomography," Optics Express 12(10):2156, 2004. The entire content of this publication is incorporated herein by reference.

Figure 2:
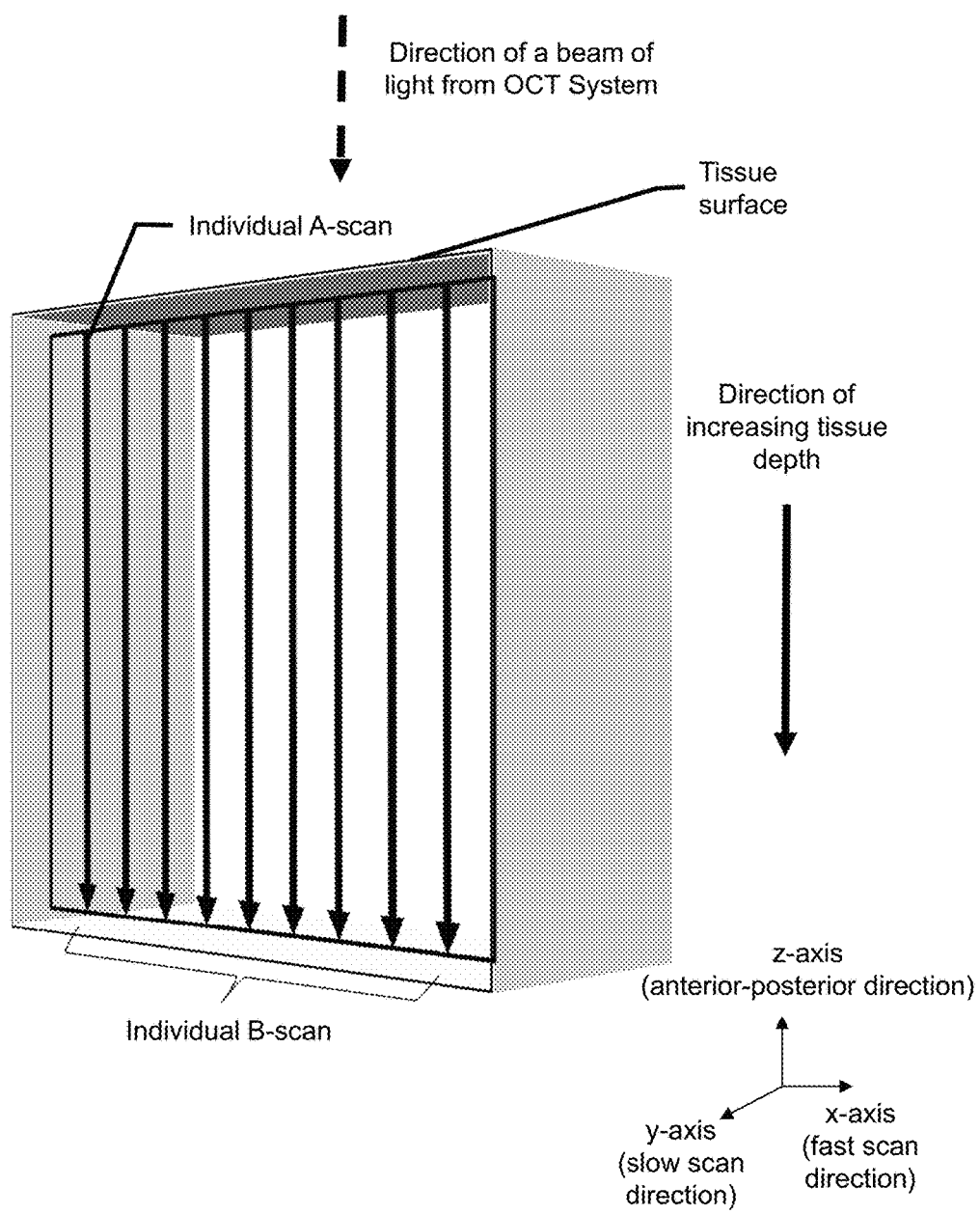
FIG. 2 schematically illustrates a scanning configuration for the OCT system.

The profile of scattering as a function of depth is called an axial scan (A-scan), as schematically shown in FIG. 2. A set of A-scans measured at neighboring locations in the physical object produces a cross-sectional image (tomogram or B-scan) of the physical object. A collection of individual B-scans collected at different transverse locations on the sample makes up a data volume or cube. Three-dimensional C-scans can be formed by combining a plurality of B-scans. For a particular volume of data, the term fast axis refers to the scan direction along a single B-scan whereas slow axis refers to the axis along which multiple B-scans are collected.

B-scans may be formed by any transverse scanning in the plane designated by the x-axis and y-axis. B-scans may be formed, for example, along the horizontal or x-axis direction, along the vertical or y-axis direction, along the diagonal of x-axis and y-axis directions, in a circular or spiral pattern, and combinations thereof. The majority of the examples discussed herein may refer to B-scans in the x-z axis directions but this disclosure may apply equally to any cross sectional image.

Figure 3:
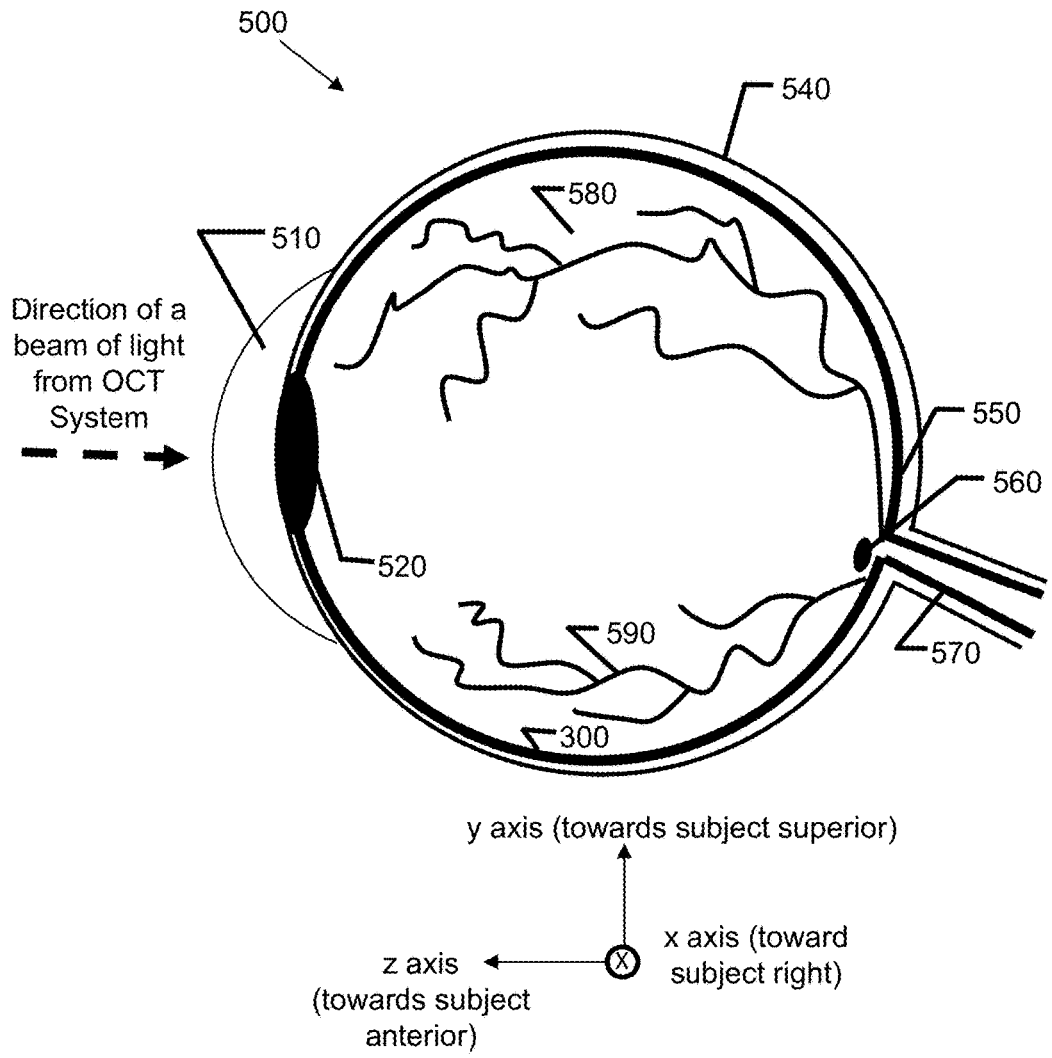
FIG. 3 schematically illustrates sagittal view of a left human eye.

The physical object 210 may be any physical object. The physical object 210 may be a human eye, 500, as shown in a simplified manner in FIG. 3. The human eye comprises a cornea 510, a pupil 520, a retina 300, a choroid 540, a fovea region 550, an optic disk 560, an optic nerve 570, a vitreous chamber 580, and retinal blood vessels 590.

Figure 4:
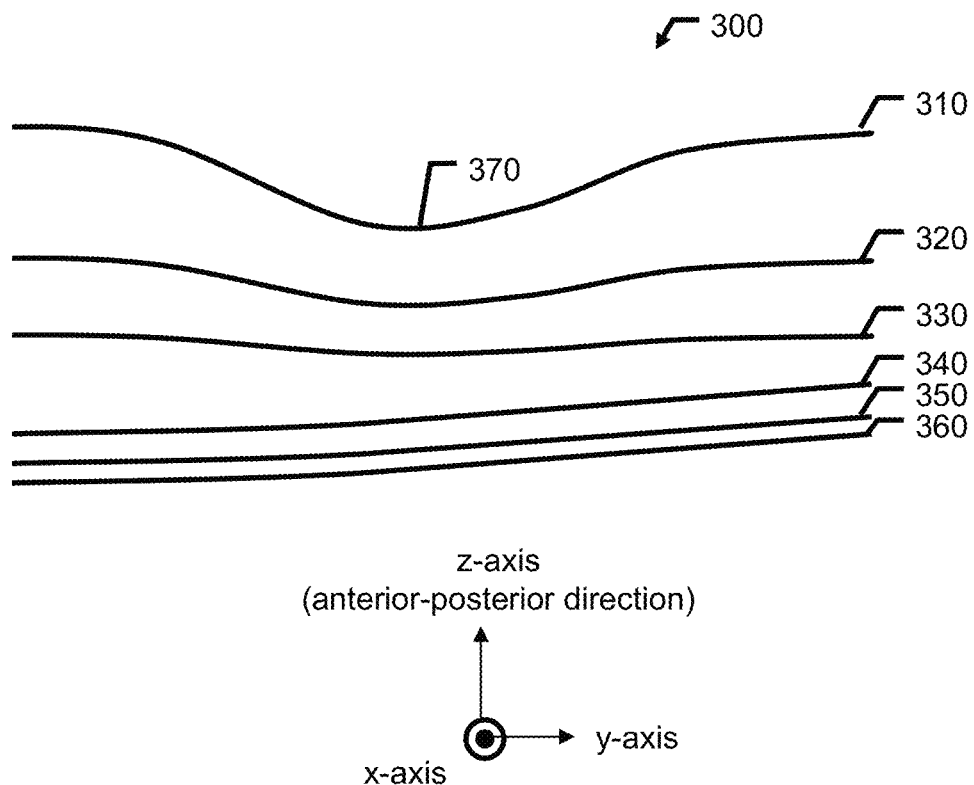
FIG. 4 schematically illustrates cross sectional layers of a retina.
Figure 5:
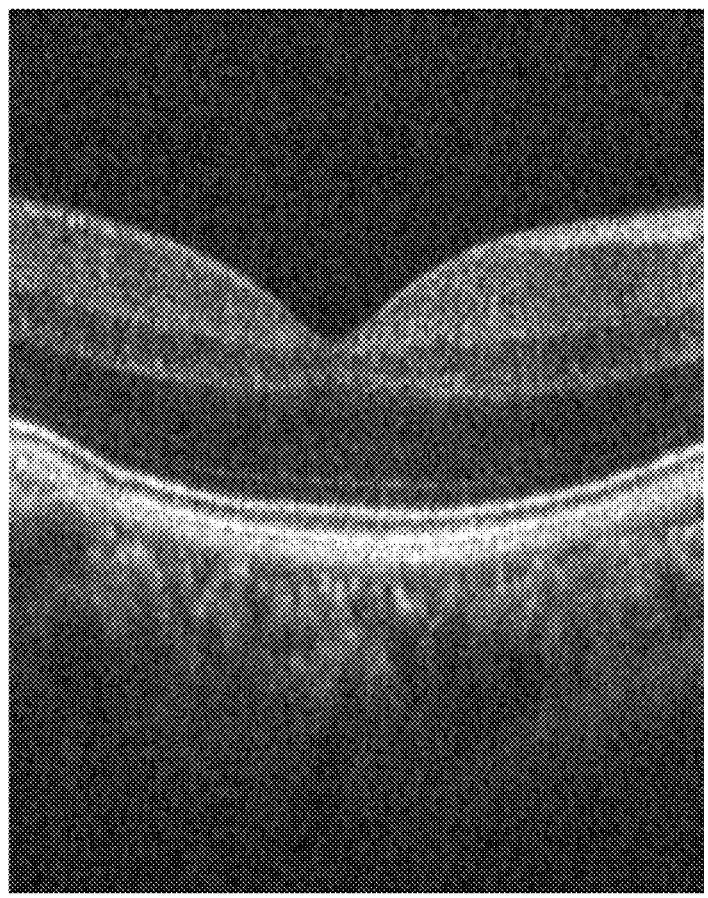
FIG. 5 shows a cross-sectional (2D) OCT image of the fovea region of the retina.
Figure 5:
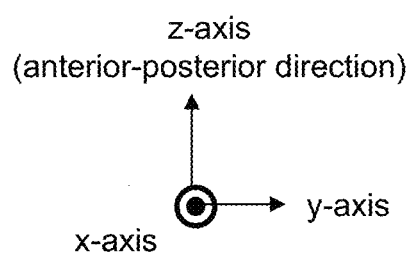

The physical object 210 may be tissue. An example of the tissue is a retina. A simplified cross-sectional image of layers of the retina 300 is schematically shown in FIG. 4. The retinal layers comprise a Nerve Fiber Layer (NFL) 310, External Limiting Membrane (ELM) 320, Inner/Outer Photoreceptor Segment 330, Outer Photoreceptor Segment 340, Retinal Pigment Epithelium (RPE) 350, Retinal Pigment Epithelium (RPE)/Bruch's Membrane Complex 360. FIG. 4 also schematically shows the fovea 370. FIG. 5 shows a cross-sectional OCT image of the fovea region of the retina.

Typical prior-art OCT methods require acquisition of multiple sequential B-scans over the same imaging location or with a small transverse displacement between B-scans in a B-scan cluster. OCT signal is then calculated based on these B-scan data within the B-scan cluster. Improved contrast within an OCT image typically involves increasing the number of scans acquired within the B-scan cluster, and thereby increasing statistics and thereby calculation time of the OCT analysis.

Repeating these calculations for series of acquired B-scan clusters across a physical object produces a three-dimensional (3D) OCT data. While 3D spatial post-processing of the OCT signal may improve the contrast, it is fundamentally limited in its effectiveness due to presence of unwanted speckle noise within the OCT data. If the imaging statistics were increased to reduce this speckle noise, this approach ultimately slows down the total vascular imaging speed with this technique, hindering its usefulness.

This disclosure relates to an OCT system that may have a configuration that calculates OCT motion contrast. The OCT system may have a configuration that calculates the OCT motion contrast by using the method described below. This disclosure relates to an OCT motion contrast method that increases the imaging speed by reducing the calculation time of the OCT analysis. This disclosure also relates to the OCT motion contrast method that minimizes effects of the speckle noise. This OCT system may provide OCT images that have image resolutions that are similar to or even better than those of the prior-art systems.

In the OCT motion contrast method, instead of using a single cluster of B-scans to calculate the OCT motion contrast, additional OCT data from neighboring sequential clusters may be used to perform the calculations. Whether or not the individual B-scans are aligned and registered in the axial (z-axis) direction, the use of data from neighboring clusters may allow for the increase of statistics for the calculations without requiring any increase in the total imaging time. The transverse resolution along the slow axis of imaging (perpendicular to the B-scan image orientation) may be reduced as a result of this method. However, the image contrast and the imaging speed may satisfy demanding needs of users.

In the OCT motion contrast method, many types of arrangements of data from multiple clusters may be combined to perform the OCT analysis, for example: (a) a window of multiple complete clusters being used in calculations (see Example 1 below) and/or (b) one complete cluster with the addition of a fraction of data from neighboring clusters (see Example 2 below).

The OCT motion contrast method may allow for clusters to be acquired and processed with even fewer B-scans than is required for typical prior-art OCT motion contrast methods, allowing for an improvement in total imaging speed (see Example 3, below).

In the OCT motion contrast method, the processed OCT data may still be able to benefit from the post-processing 3D spatial analysis typically performed on the OCT data, and may have some improved processing options, for example, due to the enhanced vascular contrast present using these methods.

The OCT motion contrast method may comprise providing at least one OCT system to acquire OCT signals to form at least one A-scan and at least one B-scan by scanning a physical object with at least one beam of light. The at least one OCT system may be any OCT system as disclosed above.

The physical object may comprise any physical object as disclosed above. The physical object has a surface and a depth. For example, a fundus of an eye has an outer surface receiving light from outside environment through pupil. The fundus of an eye also has a depth starting at and extending from its outer surface.

In this disclosure, a z-axis ("axial axis") is an axis parallel to the beam of light extending into the depth of the physical object, the x-axis and the y-axis ("transverse axes") are transverse, thereby perpendicular axes to the z-axis. Orientation of these three axes is shown in FIGS. 1-5 and 7.

Figure 6:
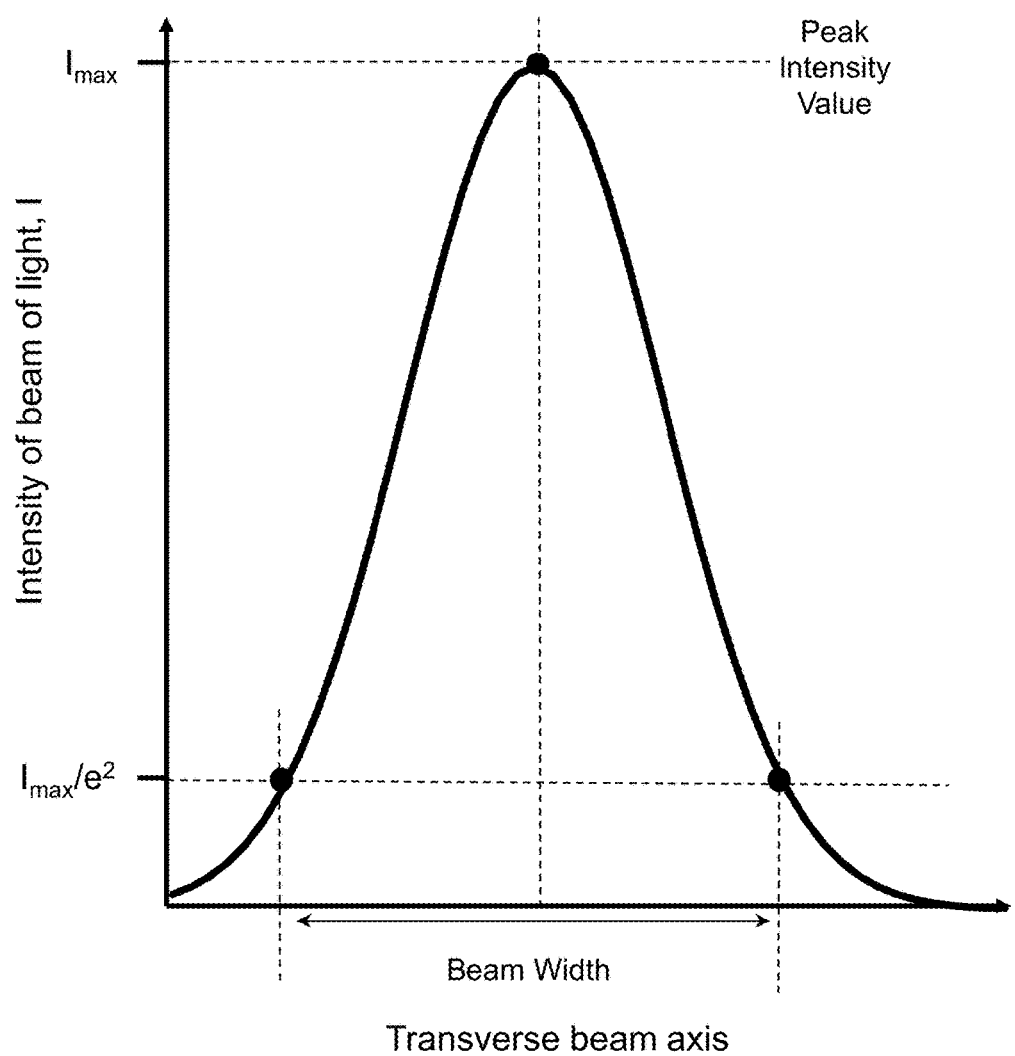
FIG. 6 shows an example of an intensity distribution of a beam of light, transverse to the propagation direction.

The at least one beam of light provided by the OCT system has a width and an intensity at a location of the physical object. This location may be at the surface of the physical object or within the physical object. In one example, at this location of the physical object, the beam of light may be focused ("focused beam of light"). For example, at this location, the width of the beam of light may be at its smallest value. Cross-sectional area of the light beam may have any shape. For example, the cross-sectional area may have circular shape or elliptic shape. The intensity of the focused beam of light varies along its transverse axis, which is perpendicular to its propagation axis. This transverse beam axis may be a radial axis. The light beam intensity at the center of the light beam is at its peak value, i.e. the beam intensity is at its maximum, and decreases along its transverse axis, forming an intensity distribution. This distribution may be approximated by a Gaussian function, as shown in FIG. 6. The width of the beam of light ("beam width") is defined as a length of line that intersects the intensity distribution at two opposite points at which the intensity is $1/e^2$ times of its peak value. The light beam may comprise more than one peak. The peak with highest beam intensity is used to calculate the beam width. An example of the beam width is schematically shown in FIG. 6. The beam width may be the focused beam of light. A typical beam width of a typical OCT system may vary in the range of 10 micrometers to 30 micrometers at the physical object location.

The OCT motion contrast method may further comprise acquiring data to form at least one B-scan cluster set. A number of at least one B-scan cluster set, P is equal to or larger than 1, wherein P is an integer. For example, P may be 1, 2, 3, 4, 5, 10, 100, 1,000, 10,000, or 100,000.

Each B-scan cluster set may comprise any number of B-scan clusters, N equal to or greater than 2, wherein N is an integer. For example, N may be 2, 3, 4, 5, 10, 100, 1,000, 10,000, or 100,000.

Each B-scan cluster may comprise any number of B-scans, M equal to or greater than 2, wherein M is an integer. For example, M may be 2, 3, 4, 5, 10, 20, 100, 1,000, 10,000, or 100,000.

Each B-scan may be located along the same transverse axis or another transverse axis (the x-axis or the y-axis) that may be parallel to those of other B-scans within the B-scan cluster set. Each B-scan may form a plane perpendicular to one of the transverse axes, and each B-scan may thereby be parallel to that of the other B-scans. That is, each B-scan may be parallel to the z-axis.

Each B-scan may comprise plurality of data points, for example, located on the (x-z) plane. Each B-scan, each B-scan cluster, and each B-scan cluster set are acquired over a period of time. That is, each B-scan, each B-scan cluster, and each B-scan cluster set are formed at a different time than all other B-scans, B-scan clusters, and B-scan cluster sets, respectively. In this disclosure, "first formed" means first formed in time; "next formed" means next formed in time; and "last formed" means last formed in time.

The OCT motion contrast may be calculated for each (x, z) data point acquired over a period of time. This motion contrast may be calculated from a complex OCT signal, OCT intensity information, phase information, or a combination thereof.

Spatial distance between each B-scan within each B-scan cluster ("intra-cluster distance") may vary in the range of 0 to a half of the beam width. For example, the intra-cluster distance may vary in the range of 0 to 15 micrometers.

Spatial distance between last formed B-scan of each B-scan cluster and first formed B-scan of next formed B-scan cluster ("inter-cluster distance") may be at least equal to or greater than 1 micrometer. For example, the intra-cluster distance may vary in the range of 1 micrometer to 10 micrometers, 1 micrometer to 100 micrometers, or 1 micrometer to 1,000 micrometers.

Figure 7:
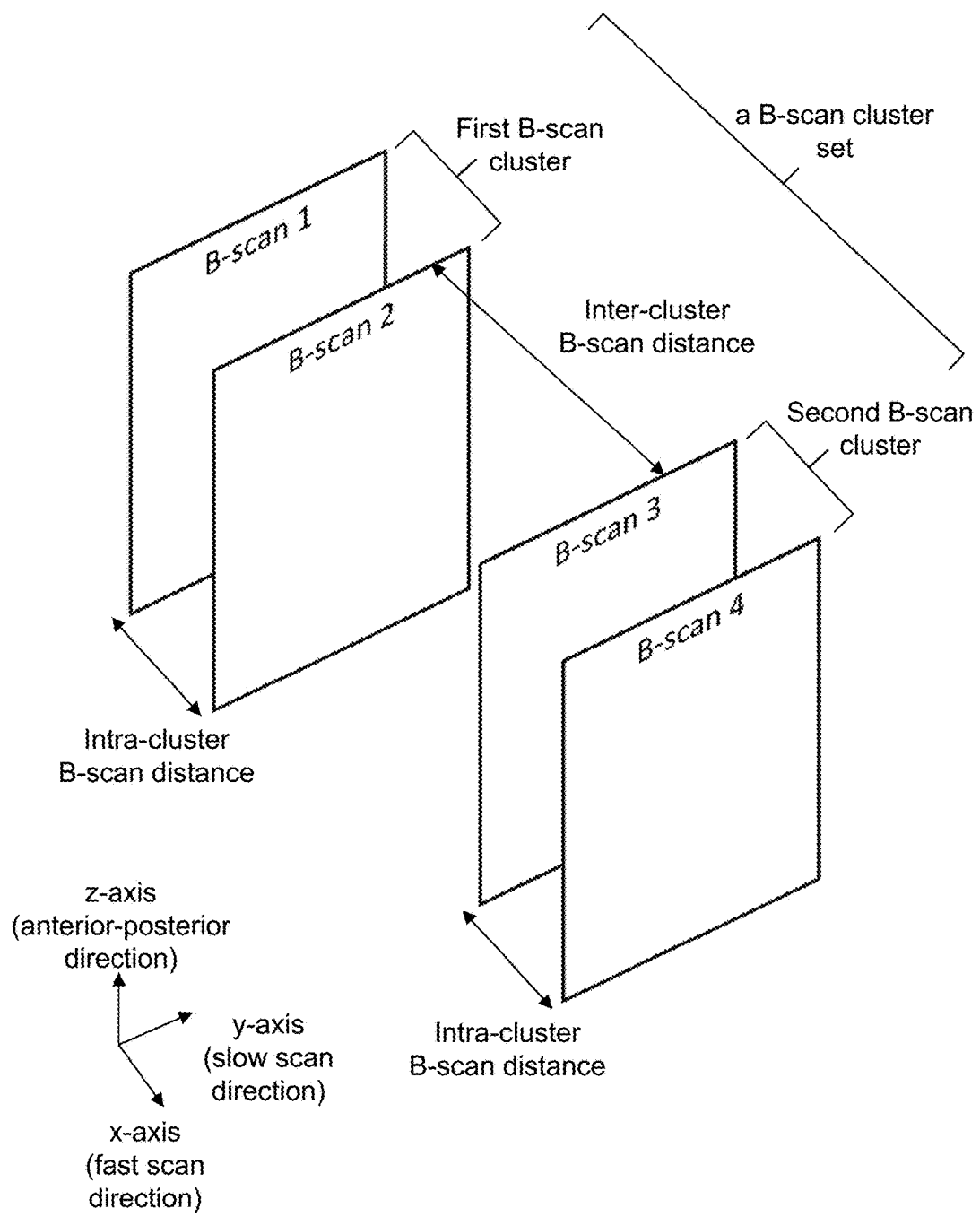
FIG. 7 schematically illustrates four B-scans, two B-scan clusters, and one B-scan cluster set by way of example that may be used for the calculation of an OCT motion contrast.

An example, shown in FIG. 7, schematically illustrates four B-scans, two B-scan clusters, and one B-scan cluster set that may be used for the calculation of an OCT motion contrast. In this example, the first B-scan cluster comprises two B-scans and the second B-scan cluster comprises two B-scans. In this example, the B-scan cluster set comprises two B-scan clusters.

The enhanced OCT processing method may further comprise acquiring data to form at least two B-scan cluster sets. Each B-scan cluster set may be located along the same transverse axis or another transverse axis (the x-axis or the y-axis) that may be parallel to those of other B-scan cluster sets.

The spatial distance between last formed B-scan of any B-scan cluster of each B-scan cluster set and first formed B-scan of any B-scan cluster of next formed B-scan cluster set ("inter-cluster-set distance") may be equal to or greater than 1 micrometer. For example, the inter-cluster-set distance may be 20 micrometers.

In one example, the spatial distance between the last formed B-scan of any B-scan cluster of each B-scan cluster set and the first formed B-scan of the next formed B-scan cluster set ("inter-cluster-set distance") may be equal to or greater than 1 micrometer. For example, the inter-cluster-set distance may be 20 micrometers.

In another example, the spatial distance between the last formed B-scan of first B-scan cluster of each B-scan cluster set and the first formed B-scan of the next formed B-scan cluster set ("inter-cluster-set distance") may be equal to or greater than 1 micrometer. For example, the inter-cluster-set distance may be 20 micrometers. The OCT system having this cluster set configuration is shown by way of example in FIG. 10 and explained in Example 4 in detail.

Yet, in another example, the spatial distance between the last formed B-scan of each B-scan cluster set and the first formed B-scan of the next formed B-scan cluster set ("inter-cluster-set distance") may be equal to or greater than 1 micrometer. For example, the inter-cluster-set distance may be 20 micrometers.

Example 1: Using a B-Scan Cluster Set Comprising Two B-Scan Clusters to Enhance OCT Motion Contrast In this example, PV-OCT method is used as the OCT motion contrast method. The phase difference between B-scans is used to calculate the statistical variance for the motion contrast. The data is acquired from two neighboring B-scan clusters, each comprising 4 B-scans. That is, there are two B-scan clusters within each B-scan cluster. Three phase changes are calculated for each B-scan cluster, with a total of 6 phase changes for the B-scan cluster set. The phase variance thus calculated is assigned to one of the neighboring pairs of the B-scans.

Typical methods would only calculate contrast from within each B-scan cluster. To achieve the same number of statistics of 6 phase changes would require 7 B-scans for each B-scan cluster, in comparison to the 4 B-scans required in this example.

Figure 8:
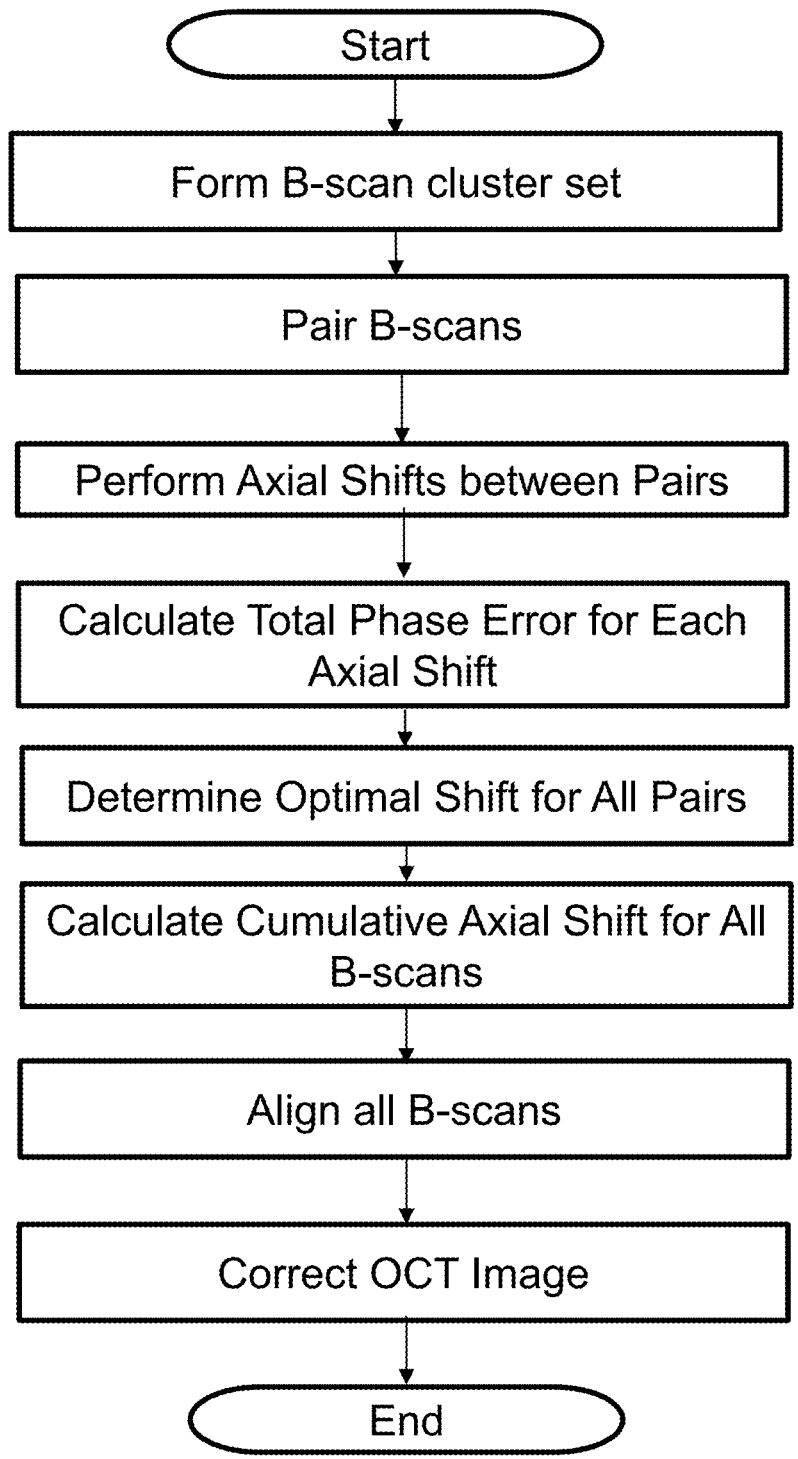
FIG. 8 shows exemplary en-face OCT images of a retinal vasculature around optic disc: (8a) OCT image formed without using the motion contrast method, (8b) OCT image formed by using the motion contrast method.
Figure 9:
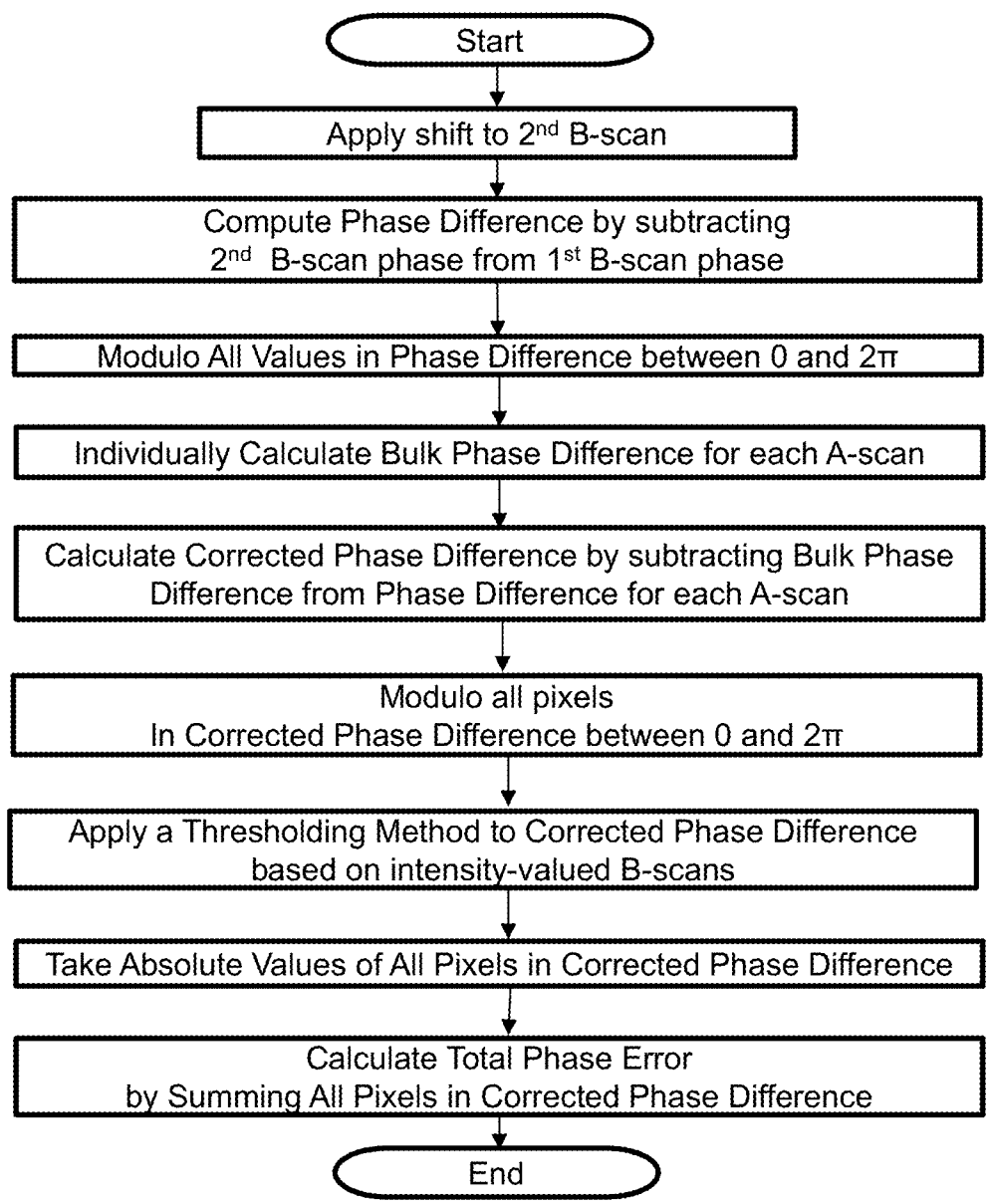
FIG. 9 shows a magnified region of the exemplary OCT images shown in FIG. 8: (9a) OCT image formed without using the motion contrast method, (9b) OCT image formed by using the motion contrast method.

Exemplary OCT images of a retinal vasculature formed by using the OCT motion contrast method disclosed in this example are compared with those formed without using this method in FIGS. 8-9. The image contrast of the magnified area shown by a white arrow in FIG. 9, obtained by the OCT motion contrast method, was similar to that obtained without using this method. These results indicate that the OCT motion contrast method, at a reduced calculation time, may yield image contrasts that are similar or even better than those of the typical methods.

Thus, using the OCT motion contrast method comprising two neighboring B-scan clusters to calculate the phase variance essentially increases the imaging speed by a factor of 7/4, while maintaining the vascular contrast available.

Example 2: Using One Complete B-Scan Cluster of Data and a Fraction of the Data from a Neighboring Cluster In this example, PV-OCT method is used as the OCT motion contrast method. The phase difference between B-scans is used to calculate the statistical variance for image contrast. The data is acquired to form two neighboring B-scan clusters, each comprising 4 B-scans. Three phase changes are calculated for one B-scan cluster and two phase changes are calculated for the other B-scan cluster. Thus, there are a total of 5 phase changes for the B-scan cluster set. The phase variance thus calculated is assigned to one of the neighboring pairs of the B-scans.

In this example, not all B-scans in each cluster are used in the phase change calculations, although they are acquired for each cluster. This exemplary method reduces calculation time for the phase variance by a factor of 6/5 as compared to that disclosed in Example 1.

Thus, the imaging speed may further be increased by using every B-scan for one B-scan cluster and a fraction of number of B-scans for the next formed cluster to calculate an OCT signal.

Example 3

In this example, the intensity variance is calculated to form an OCT image. Typical intensity variance imaging methods may require a minimum of 4 B-scans in each B-scan cluster to perform 3 phase change calculations.

However, in the OCT motion contrast method, a B-scan cluster set comprising two B-scan clusters comprising three B-scans per B-scan cluster may provide similar OCT motion contrast as follows. In this example, since each B-scan cluster provides 2 phase change calculations, there are total of 4 phase change calculations available for outlier analysis and motion contrast calculations. Thus, the required number of B-scans per cluster may be reduced from 4 to 3 by using the OCT motion contrast method disclosed above.

Example 4

Figure 10:
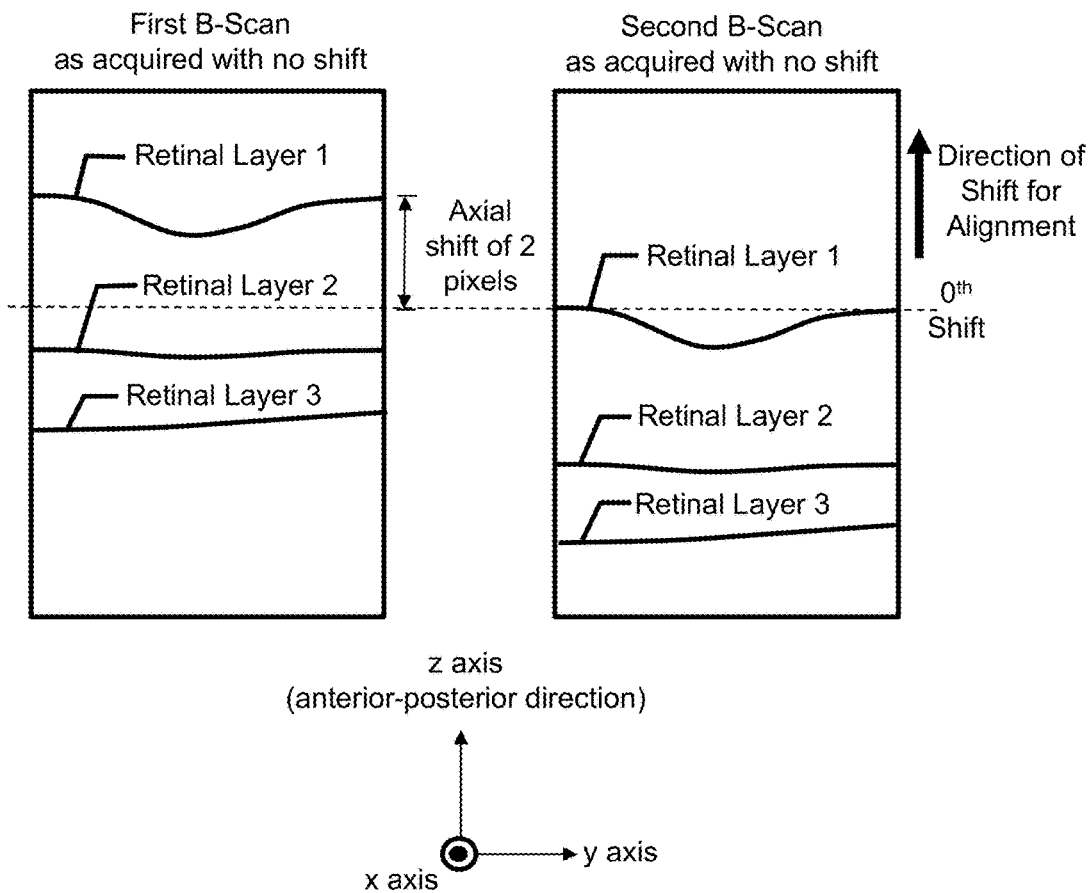
FIG. 10 shows an example of construction of P number of B-scan cluster sets that may be used to obtain P number of cross-sectional OCT images of the physical object.
Figure 11:
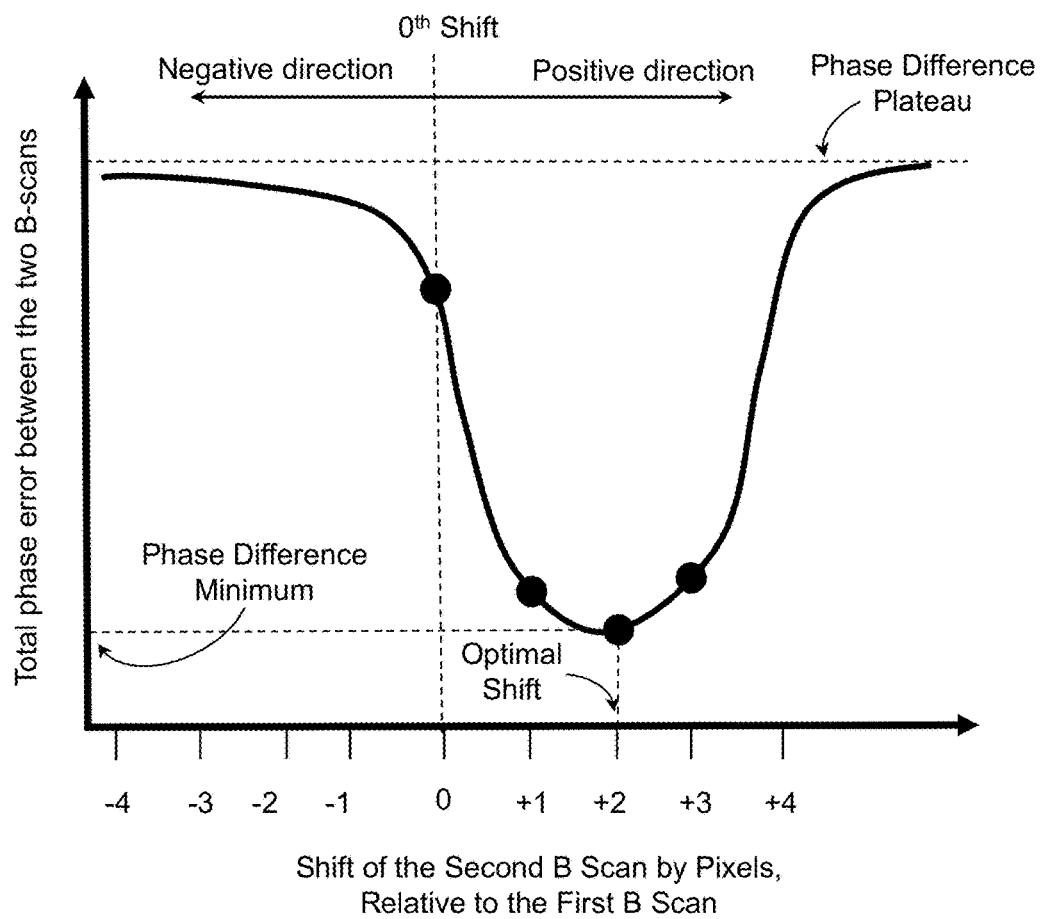

In this example, the OCT system is configured to form P number of B-scan cluster sets, as shown in FIG. 10. There are N number of B-scan clusters. Each B-scan cluster set has 4 B-scan clusters, and each B-scan cluster has 4 B-scans. That is, there are 4 B-scan clusters within each B-scan cluster set, and 4 B-scans within each B-scan cluster.

First B-scan cluster set has four B-scan clusters 1, 2, 3 and 4; second B-scan cluster set has four B-scan clusters 2, 3, 4 and 5; third B-scan cluster set has four B-scan clusters 3, 4, 5 and 6, $P^{th}$ B-scan cluster set has four B-scan clusters N–3, N–2, N–1 and N.

In this example, the inter-cluster-set distance between the last formed B-scan of the first formed B-scan cluster of each B-scan cluster set and the first formed B-scan of the next formed B-scan cluster set is about 10 micrometers. Inter-cluster distance is about 10 micrometers. The intra-cluster distance is 0.5 micrometers.

In this example, all B-scans of each cluster set, i.e. 16 B-scans are used for the OCT calculations. Three phase changes are calculated for each B-scan cluster, with a total of 12 phase changes for each B-scan cluster set.

In this example, the OCT systems has a configuration that calculates OCT motion contrast for each B-scan cluster set; and registers the calculated OCT motion contrast as the OCT motion contrast of first B-scan cluster of each B-scan cluster set. For example, the four B-scan clusters 1, 2, 3 and 4 of the first B-scan cluster set are used to calculate a motion contrast and the calculated motion contrast is registered as the OCT motion contrast of B-scan cluster 1; the four B-scan clusters 2, 3, 4 and 5 of the second B-scan cluster set are used to calculate a motion contrast and the calculated motion contrast is registered as the OCT motion contrast of B-scan cluster 2; the four B-scan clusters 3, 4, 5 and 6 of the third B-scan cluster set are used to calculate a motion contrast and the calculated motion contrast is registered as the OCT motion contrast of B-scan cluster 3; . . . the four B-scan clusters N–3, N–2, N–1 and N of the $P^{th}$ B-scan cluster set are used to calculate a motion contrast and the calculated motion contrast is registered as the OCT motion contrast of B-scan cluster N–3.

These calculations yield a P number of cross sectional OCT images of the physical object with motion contrast.

Example 5

This disclosure also relates to identification and reduction of noise effects to improve signal to noise ratio of the motion contrast calculations ("noise reduction method"). The enhanced OCT processing method may further comprise reducing effects of noisy data on the motion contrast calculations. The noisy data may be caused by sample motion happened during the data acquisition. The noisy data may also be caused by components of the OCT system such as detectors, light sources and scanner optics. This reduction may be achieved by outlier analysis.

The noise reduction method may use a thresholding method and/or a weighting method to reduce effects of noise. In the thresholding approach, data that have values higher or lower than a predetermined value (i.e. thresholding criteria) is removed from the calculations. In the weighting approach, data that have values higher or lower than a predetermined value (i.e. weighting criteria) is incorporated into the calculations, but with a reduced influence. Such approaches may comprise using a threshold based on noise performance, using a threshold on factors other than the noise performance, weighting data measurements before the motion contrast calculation, and a combination thereof.

For example, the noise reduction method may comprise removing a noisiest data from the calculations. Examples of such methods may be:

(a) "B-scan outlier analysis method" comprises comparing changes among B-scans in each cluster, wherein the B-scans are acquired over time t. This particular method relates to overall noise/decorrelation performance on the scale of the B-scans. This method may comprise forming B-scan pairs within a B-scan cluster, wherein B-scans in each B-scan pair comprise two proximate B-scans; identifying a B-scan pair that has highest overall motion noise, phase noise, and/or decorrelation as compared to that of other B-scan pairs; and removing the data point that has highest overall motion noise, phase noise, and/or decorrelation from calculations. Most physical motion may be identified and its effects may be removed by using the B-scan outlier analysis method, since typical motion of the physical object may relatively be consistent over time scales of the B-scan acquisitions.

(b) "A-scan outlier analysis method" comprises comparing changes among sequential A-scans in each B-scan cluster, wherein sequential A-scans are acquired at the same location on the x-z plane over time t. This particular method relates to overall noise/decorrelation performance on the scale of the A-scans. This method comprises forming B-scan pairs within a B-scan cluster, wherein B-scans in each B-scan pair comprise two proximate B-scans; forming A-scan pairs by selecting one A-scan from each B-scan, wherein the A-scan pair comprises two A-scans that are acquired at the same location on the x-z plane over a period; identifying the A-scan pair that has the highest overall motion noise, phase noise, or decorrelation as compared to that of other A-scan pairs; and removing the data points of said A-scan pair(s) from calculations. Noise caused by hardware-created motion, such as quick, unwanted deviations of the scanning light position due to the scanners in the OCT system may be identified and its effects may be removed by using the A-scan outlier analysis method.

(c) "Data point outlier analysis method" comprises comparing changes among data points in each cluster, wherein sequential data points are acquired at the same (x, z) location on the x-z plane over time t. This particular method relates to the noisiest data points. In this method, data points that have the highest noise (as compared to other data points acquired at the same (x, z) location on the x-z plane within a B-scan cluster over time t) are identified and removed from the calculations. Noise caused by speckle due to motion of the physical object may be identified and its effects may be removed by using the data point outlier analysis method.

(d) "Method of data point outlier analysis based on B-scan intensity" may comprise calculating intensities of two sequential B-scans, calculating a minimum value or an average value of intensities of two sequential B-scans in a B-scan cluster; identifying at least one data point that have average value or minimum value intensities from the two sequential B-scans which is lower than a chosen thresholding value; and removing said data point(s) from calculations. As a result, noisiest data points may be removed from each B-scan and the remaining data points may be used in the motion contrast calculations. Effects of detector noise or shot noise may be removed by using the method of data point outlier analysis based on B-scan intensity.

All calculated or acquired data may need to be kept for the motion contrast calculations. For example, the noisiest data may be close to the thresholding value and thereby be included in the motion contrast calculations. For such cases, the weighting approaches may be used to reduce influence of the noisiest data to the motion contrast calculations. Examples such methods may be:

(e) "Method of weighting results from other clusters". The motion contrast may degrade with the use of additional statistics from proximate B-scan clusters, this effect may be reduced by giving the calculations from different B-scan clusters within a B-scan cluster set different weighting factors. For example, the first cluster can have a weighting factor (i.e. weighting criteria) of 1 and all proximate B-scan clusters within the B-scan cluster set have a weighting factor of ½.

(f) "Method of weighting results based on overall noise". Spurious data is more likely to occur during instances of overall system noise in the images (on a B-scan or an A-scan). In this method, B-scans or A-scans may be used to identify the noise to have a weighting factor and influences of the noisiest data may be reduced by using the weighting factor.

A combination of above methods summarized in (a) to (f) may be used to identify and reduce effects of noise.

The OCT motion contrast method disclosed above may be used for any OCT related application. For example, this method maybe used in forming larger field of view OCT images of the physical object. This method may be incorporated into methods and systems related to OCT based angiography. For example, the choroidal vasculature may be identified in more detail by using the OCT motion contrast method. The OCT methods comprising the OCT motion contrast method also be used in diagnosis and/or treatment of health conditions such as diseases. For example, the OCT methods comprising the OCT motion contrast method may be used in characterization of retinal health.

The OCT system disclosed above may provide any information related to the physical object. For example, this system, which may uses the motion contrast method, may provide 2D (i.e. cross-sectional) images, en-face images, 3-D images, metrics related to a health condition, and the like. This system may be used with any other system. For example, the OCT system may be used with an ultrasound device, or a surgical system for diagnostic or treatment purposes. The OCT system may be used to analyze any physical object. For example, the OCT system may be used in analysis, e.g. formation of images, of, for example, any type of life forms and inanimate objects. Examples of life forms may be animals, plants, cells or the like.

Unless otherwise indicated, the processing unit 140 that has been discussed herein may be implemented with a computer system configured to perform the functions that have been described herein for this unit. The computer system includes one or more processors, tangible memories (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

The computer system for the processing unit 140 may include one or more computers at the same or different locations. When at different locations, the computers may be configured to communicate with one another through a wired and/or wireless network communication system.

The computer system may include software (e.g., one or more operating systems, device drivers, application programs, and/or communication programs). When software is included, the software includes programming instructions and may include associated data and libraries. When included, the programming instructions are configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

Any combination of methods, devices, systems, and features disclosed above are within the scope of this disclosure.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

In this disclosure, the indefinite article "a" and phrases "one or more" and "at least one" are synonymous and mean "at least one".

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. An optical coherence tomography (OCT) system having a configuration that:
   scans a physical object, which has a surface and a depth, with a beam of light that has a beam width and a direction;
   acquires OCT signals from the scan;
   forms at least one B-scan cluster set using the acquired OCT signals such that:
      each B-scan cluster set includes at least two B-scan clusters;
      each B-scan cluster includes at least two B-scans;
      the B-scans within each B-scan cluster set are parallel to one another and parallel to the direction of the beam of light;
      each B-scan, each B-scan cluster, and each B-scan cluster set are formed at a different time than all other B-scans, B-scan clusters, and B-scan cluster sets, respectively;
      each B-scan within each B-scan cluster is separated from any next formed B-scan within that B-scan cluster by a distance ("intra-cluster distance") in the range of 0 to half of the beam width;
      the last formed B-scan within each B-scan cluster is separated from the first formed B-scan within any next formed B-scan cluster ("inter-cluster distance") by at least one micrometer; and
   uses all or a fraction of the B-scans within each B-scan cluster set to calculate OCT motion contrast for each B-scan cluster set; and
   registers the calculated OCT motion contrast as the OCT motion contrast of one of the B-scan clusters within each B-scan cluster set.

2. The OCT system of claim 1, wherein:
   the OCT system has a configuration that forms at least two B-scan cluster sets parallel to one another using the acquired OCT signals, and
   last formed B-scan of one of the B-scan clusters of each B-scan cluster set is separated from first formed B-scan of one of the B-scan clusters of next formed B-scan cluster set ("inter-cluster-set distance") by at least one micrometer.

3. The OCT system of claim 1, wherein:
   the OCT system has a configuration that forms at least two B-scan cluster sets parallel to one another using the acquired OCT signals, and
   the last formed B-scan of one of the B-scan clusters of each B-scan cluster set is separated from the first formed B-scan of the next formed B-scan cluster set ("inter-cluster-set distance") by at least one micrometer.

4. The OCT system of claim 1, wherein:
   the OCT system has a configuration that forms at least two B-scan cluster sets parallel to one another using the acquired OCT signals, and
   the last formed B-scan of first formed B-scan cluster of each B-scan cluster set is separated from the first formed B-scan of the next formed B-scan cluster set ("inter-cluster-set distance") by at least one micrometer.

5. The OCT system of claim 1, wherein
   the OCT system has a configuration that forms at least two B-scan cluster sets parallel to one another using the acquired OCT signals, and
   the last formed B-scan of each B-scan cluster set is separated from the first formed B-scan of the next formed B-scan cluster set ("inter-cluster-set distance") by at least one micrometer.

6. The OCT system of claim 1, wherein the number of B-scan clusters within each B-scan cluster set is 2, 3 or 4.

7. The OCT system of claim 1, wherein the OCT system has a configuration that uses all of the B-scans within all of the B-scan clusters to calculate the OCT motion contrast.

8. The OCT system of claim 1, wherein the OCT system has a configuration that uses all of the B-scans within at least one of the B-scan clusters and only a fraction of the B-scans within at least one other of the B-scan clusters to calculate the OCT motion contrast.

9. The OCT system of claim 1, wherein the inter-cluster distance is no more than 100 micrometers.

10. The OCT system of claim 1, wherein the inter-cluster distance is no more than 50 micrometers.

11. The OCT system of claim 2, wherein the inter-cluster-set distance is no more than 100 micrometers.

12. The OCT system of claim 2, wherein the inter-cluster-set distance is no more than 50 micrometers.

13. The OCT system of claim 1, wherein the OCT system has a configuration that reduces one or more effects of noise on OCT motion contrast by using a thresholding method or a weighting method before calculating the OCT motion contrast.

14. The OCT system of claim 13, wherein the OCT system has a configuration that uses the thresholding method before calculating the OCT motion contrast and wherein the thresholding method includes:
   forming pairs of proximate B-scans within one of the B-scan clusters;
   identifying the B-scan pair that has highest overall motion noise, phase noise, or decorrelation as compared to that of the other B-scan pairs; and
   removing a data point that has the highest overall motion noise, phase noise, or decorrelation from the calculation of the OCT motion contrast.

15. The OCT system of claim 13, wherein the OCT system has a configuration that uses the thresholding method before calculating the OCT motion contrast and wherein the thresholding method includes:
   forming pairs of proximate B-scans within one of the B-scan clusters;
   forming pairs of A scans at the same location on a plane parallel to the direction of the beam of light, each member of the pair being selected from a different B scan;

identifying the A-scan pair that has the highest overall motion noise, phase noise, or decorrelation as compared to that of other A-scan pairs; and removing data points of the identified A-scan pair from the calculation of the OCT motion contrast.

16. The OCT system of claim 13, wherein the OCT system has a configuration that uses the thresholding method before calculating the OCT motion contrast and wherein the thresholding method includes:

comparing changes among data points in each B scan cluster that are sequentially acquired at the same location on a plane parallel to the direction of the beam;

identifying at least one data point that has the highest noise as compared to the other data points acquired at the same location on the plane within each B-scan cluster; and removing the identified at least one data point from the calculation of the OCT motion contrast.

17. The OCT system of claim 13, wherein the OCT system has a configuration that uses the thresholding method before calculating the OCT motion contrast and wherein the thresholding method includes:

calculating intensities of two sequentially formed B-scans within a B-scan cluster;

calculating a minimum value or an average value of the intensities;

identifying at least one data point that has an average value or a minimum value of intensities from the two sequentially formed B-scans which is lower than a thresholding value; and removing the at least one identified data point from the calculation of OCT motion contrast.

18. The OCT system of claim 13, wherein the OCT system has a configuration that uses the weighting method and wherein the weighting method includes reducing effects of at least one noisy B-scan cluster by using a weighting criterion.

19. The OCT system of claim 13, wherein the OCT system has a configuration that uses the weighting method before calculating the OCT motion contrast and wherein the weighting method includes using at least one B-scan or at least one A-scan within a B-scan cluster, thereby identifying noisy data, and reducing one or more effects of the noisy data by using a weighting criterion.

20. The OCT system of claim 1, wherein the OCT system has a configuration that uses the calculated OCT motion contrast to form an image of the physical object.

21. The OCT system of claim 1, wherein the physical object is human tissue.

22. The OCT system of claim 1, wherein the OCT system has a configuration that identifies regions of motion based on intensity or phase variations between the B-scans.

23. The OCT system of claim 22, wherein the OCT system has a configuration that identifies the regions of motion using a Phase Variance OCT (PV-OCT) method, a Phase Contrast OCT (PC-OCT) method, an Intensity/Speckle Variance OCT (IV-OCT) method, a Doppler OCT (D-OCT) method, a Power of Doppler Shift OCT (PDS-OCT) method, a Split Spectrum Amplitude Decorrelation Analysis (SSADA) method, an Optical Micro-angiography (OMAG) method, a Correlation Mapping OCT (cmOCT) method, or a combination thereof.

24. The OCT system of claim 22, wherein OCT system has a configuration that uses a Phase Variance OCT (PV-OCT) method.

25. The OCT system of claim 1, wherein the OCT system comprises:

at least one light source that provides that provides the beam of light;

at least one retro-reflector;

at least one optical fiber coupler or at least one free space coupler that guides the beam of light to the physical object and to at least one retro-reflector, wherein the beam of light guided to the physical object forms at least one backscattered light beam, and wherein the beam of light guided to the at least one retro-reflector forms at least one reflected reference light beam;

at least one scanning optic that scans the at least one light beam over the physical object;

at least one detector that:
combines the at least one backscattered light beam and the at least one reflected light beam to form light interference,
detects magnitude and time delay of the at least one backscattered light beam, and
forms at least one OCT signal;

wherein the at least one optical fiber coupler or the at least one free space coupler guides the at least one backscattered light beam and the at least one reflected light beam to the at least one detector;

at least one processor that obtains and analyzes the at least one OCT signal formed by the at least one detector, and forms an image of the physical object; and at least one display that displays the image of the physical object.

26. Non-transitory, tangible, computer-readable storage media containing a program of instructions that causes a computer system running the program of instructions to function as an optical coherence tomography (OCT) system, including to:

scan a physical object, which has a surface and a depth, with a beam of light that has a beam width and a direction;

acquire OCT signals from the scan;

form at least one B-scan cluster set using the acquired OCT signals such that:
each B-scan cluster set includes at least two B-scan clusters;
each B-scan cluster includes at least two B-scans;
the B-scans within each B-scan cluster set are parallel to one another and parallel to the direction of the beam of light;
each B-scan, each B-scan cluster, and each B-scan cluster set are formed at a different time than all other B-scans, B-scan clusters, and B-scan cluster sets, respectively;
each B-scan within each B-scan cluster is separated from any next formed B-scan within that B-scan cluster by a distance ("intra-cluster distance") in the range of 0 to half of the beam width; and
the last formed B-scan within each B-scan cluster is separated from the first formed B-scan within any next formed B-scan cluster ("inter-cluster distance") by at least one micrometer;

use all or a fraction of the B-scans within each B-scan cluster set to calculate OCT motion contrast for each B-scan cluster set; and register the calculated OCT motion contrast as the OCT motion contrast of one of the B-scan clusters within each B-scan cluster set.

27. The storage media of claim 26 wherein the program of instructions causes the computer system running the program of instructions to:

obtain and analyze at least one of the OCT signals;

form an image of the physical object; and
display the image of the physical object.

\* \* \* \* \*